US005578708A

United States Patent [19]

Okazaki et al.

[11] Patent Number: 5,578,708

[45] Date of Patent: Nov. 26, 1996

[54] BONE-ASSOCIATED TRANSCRIPTION CONTROL FACTOR-LIKE PROTEIN

[75] Inventors: Makoto Okazaki, Kawagoe; Sunao Takeshita, Tsu; Shinji Kawai, Iruma-gun; Reiko Kikuno, Tokorozawa, all of Japan; Egon Amann, Marburg, Germany

[73] Assignee: Hoechst Japan Limited, Tokyo, Japan

[21] Appl. No.: 208,108

[22] Filed: Mar. 8, 1994

[30] Foreign Application Priority Data

Mar. 10, 1993 [JP] Japan .................................... 5-048875

[51] Int. Cl.[6] .................................................... C07K 14/51

[52] U.S. Cl. ............................ 530/399; 530/350; 930/10

[58] Field of Search .................................... 530/399, 350; 514/12; 435/69.4; 930/10

[56] References Cited

U.S. PATENT DOCUMENTS 5,460,951 10/1995 Kawai et al. .......................... 435/69.1

OTHER PUBLICATIONS

Gieffers et al. (1993) *Euro. J. of Cell Biol.* 62(2):352–361.

Katoh et al. (1992) *DNA and Cell Biol.* 11(10):735–743.

Kawai et al. (1994) *J. Biochem.* 115:641–643.

Takamatsu et al. (1992) *Biochem. Biophys. Res. Comm.* 185(1):224–230.

Takeshita et al. (1993) *Biochem. J.* 294:271–278.

Tezuka et al. (1990) *Biochem. Biophys. Res. Comm.* 173(1):246–251.

*Primary Examiner*—Stephen G. Walsh

*Attorney, Agent, or Firm*—Finnegan, Henderson, Farabow, Garrett & Dunner, L.L.P.

[57] ABSTRACT

Bone-associated proteins derived from bone of mammals, including mice and human beings, named OSF-6. The protein is the novel natural type mammal protein, which can play an important role in bone formation, and belongs to a group of transcription control factors.

OSF-6 can be used as a therapeutic agent for bone metabolic diseases, and also as a diagnostic agent for bone metabolic diseases, since it may demonstrate a high organ specificity to bone.

1 Claim, 4 Drawing Sheets

Fig. 2

```
           128                                                      170
mOSF-6     CDGCN.GPVV GTRYKCSVCP DYDLCSVC.. ..EGKGLHRE HSKLIFPN
ref2(P)    CDGCGLAPLI GFRYKCVQCS NYDLCQKC.. ..ELAHKHPE HLMLRMPT
ADA2       CDVCSADCTN RVRVSCAICP EYDLCVPCFS QGSYTGKHRP YHDYRIIE
Consensus  CD-C------ --R--C--C- -YDLC--C-- -------H-- --------
```

Fig. 3

```
           392                                                    442
mOSF-6     ADPRLIESLS QMLSMGFSDE GGWLTRLLQT KNYDIGAALD TIQYSKHPPP L
ref2(P)    TDESINKSIH AMMAMGFSNE GAWLTQLLES VQGNISAALD VMNVSQNRN. .
Consensus  -D-----S-- -M--MGFS-E G-WLT-LL-- ----I-AALD ----S----- -
```

1 Thymus

2 Spleen

3 Brain

4 Kidney

5 Liver

6 Lung

7 Testis

8 Heart

9 Concentrated cell mixture of osteoblasts originating in the calvaria

10 Cells from 3rd day culture of MC3T3-E1 cells

11 Cells from 12th day culture of MC3T3-E1 cells

12 Cells from 60th day culture of MC3T3-E1 cells

13 NIH3T3 cells

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 2005 base pairs
( B ) TYPE: nucleic acid
( C ) STRANDEDNESS: single
( D ) TOPOLOGY: linear ( i i ) MOLECULE TYPE: cDNA to mRNA ( v i ) ORIGINAL SOURCE:
( A ) ORGANISM: Mus musculus
( H ) CELL LINE: Osteoblast MC3T3E1

( x i ) SEQUENCE DESCRIPTION: SEQ ID NO:1:

-continued

```
GTCCGTACCT AGACCGCGGT TATGGCGTCG TTCACGGTGA AGGCCTATCT TCTGGGCAAG   60
GAGGAGGCGA CCCGCGAGAT CCGCCGCTTC AGCTTCTGCT TCAGCCCGGA GCCGGAGGCG  120
GAAGCCCAAG CCGCGGCCGG CTCGGGGCCC TGCGAGAGGC TGCTGAGCCG AGTGGCTGTG  180
CTGTTCCCCA CGCTGAGGCC TGGCGGCTTC CAGGCGCACT ACCGCGATGA GGATGGGGAC  240
TTGGTTGCCT TTTCCAGTGA TGAGGAGCTG ACAATGGCTA TGTCCTATGT GAAAGATGAC  300
ATCTTCCGCA TCTACATTAA AGAGAAGAAG GAGTGCCGGC GGGAACATCG CCCACCATGT  360
GCTCAGGAGG CACCCCGAAA CATGGTGCAC CCCAATGTGA TCTGTGATGG TTGCAACGGG  420
CCTGTGGTGG GAACTCGCTA TAAGTGCAGT GTGTGCCCAG ACTACGACCT GTGCAGCGTG  480
TGCGAGGGGA AGGGCCTGCA CAGGGAACAC AGCAAGCTCA TCTTTCCCAA CCCCTTTGGC  540
CACCTCTCTG ATAGCTTCTC TCATAGCCGC TGGCTTCGGA AGCTGAAACA TGGACACTTT  600
GGCTGGCCTG GCTGGGAGAT GGGCCCACCG GGGAACTGGA GCCCACGTCC TCCTCGTGCA  660
GGGGATGGCC GCCCTTGCCC TACAGCTGAG TCAGCTTCTG CTCCACCAGA AGATCCCAAT  720
GTCAATTTCC TGAAGAATGT GGGGGAGAGT GTGGCAGCTG CCCTCAGCCC TCTAGGCATT  780
GAGGTTGACA TTGATGTGGA ACATGGAGGG AAGAGAAGCC GCCTGACACC CACTACCCCA  840
GAAAGTTCCA GCACAGGCAC AGAAGACAAG AGTAACACTC AGCCAAGCAG CTGCTCTTCG  900
GAAGTCAGCA AACCTGACGG GGCTGGGGAG GGCCCTGCTC AGTCTCTGAC AGAGCAAATG  960
AAAAAGATAG CCTTGGAGTC GGTGGGACAG CCAGAGGAAC AGATGGAGTC GGGAAACTGC 1020
TCAGGAGGAG ACGATGACTG GACACATTTG TCTTCAAAAG AAGTGGACCC ATCTACAGGT 1080
GAACTCCAGT CTCTACAGAT GCCAGAATCG GAAGGGCCAA GCTCTCTAGA CCCCTCACAG 1140
GAAGGACCCA CAGGGCTGAA GGAAGCTGCC CTATACCCAC ATCTCCCACC AGAGGCTGAT 1200
CCCCGGCTGA TTGAGTCCCT CTCCCAGATG CTGTCCATGG GTTTCTCGGA TGAAGGCGGC 1260
TGGCTCACCA GGCTCCTACA GACCAAGAAT TACGACATCG GGGCTGCTCT GGACACGATC 1320
CAGTATTCGA AGCACCCTCC ACCATTGTGA TAGTGCTGTG GCCAAGCCCC ACCCCCTTTG 1380
TCTTGTAGTT GCATCACGTA GAGCAGCAGG GCTTCTATAG ATAGGCCCAG TGTCTTGGCA 1440
TTCTTGTAGA ATCTTCAGGT GGGAATGTGT GATGCCTTTT CAGGCAATAG GAAAGTGCAT 1500
GAGGAGAGTT TTGAATGTGC ATATGCTGAC GCCTGAGAAC AGACCCAGGT ACCCGTGGCT 1560
GAGCTGAGCT TCCTCTGCTT TCCCTAGGCC TGGCCTCTGC AGGGAACTGC AGCACACACT 1620
GCACTCCCAC CTGCTCTTGC CGCCAGCATT GCACCAGCAG TCCAGAATTC CTGCCTGACA 1680
ACCCGTGTTT CCTTTATTAA AAGTGATTAG TACAACTGCT AGTTATTTTC AACAAATAAA 1740
GCCATTATGT TAAGAGGGGA CTGTCCATAG TGAGTGAAAG GTGGCAGGCA GGGGCCTACA 1800
GCTCCTAGGG AATGGAGAAT TCATGTGAAG CCGAATGAAG GATCTTATCT TATACTGTCC 1860
CCCTTTCTAA TGGCCACTCT TTAGTGTTTG TGTCTAATGT TAATGCTTAA AGCACAGGAC 1920
CCCCATGTAG CTTCCTCTGA CTTGGTTTGT AAGTAACCTG TAATAAAATG GCATATGCAC 1980
TTTAAAAAAA AAAAAAAAAA AAAAA                                        2005
```

( 2 ) INFORMATION FOR SEQ ID NO:2:

( i ) SEQUENCE CHARACTERISTICS:
( A ) LENGTH: 442 amino acids
( B ) TYPE: amino acid
( D ) TOPOLOGY: linear ( i i ) MOLECULE TYPE: peptide ( v i ) ORIGINAL SOURCE:
( A ) ORGANISM: Mus musculus -continued ( H ) CELL LINE: Osteoblast MC3T3E1

( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ala | Ser | Phe | Thr | Val | Lys | Ala | Tyr | Leu | Leu | Gly | Lys | Glu | Glu | Ala |
| 1 | | | | 5 | | | | | 10 | | | | | 15 | |
| Thr | Arg | Glu | Ile | Arg | Arg | Phe | Ser | Phe | Cys | Phe | Ser | Pro | Glu | Pro | Glu |
| | | | 20 | | | | | 25 | | | | | 30 | | |
| Ala | Glu | Ala | Gln | Ala | Ala | Ala | Gly | Ser | Gly | Pro | Cys | Glu | Arg | Leu | Leu |
| | | 35 | | | | | 40 | | | | | 45 | | | |
| Ser | Arg | Val | Ala | Val | Leu | Phe | Pro | Thr | Leu | Arg | Pro | Gly | Gly | Phe | Gln |
| | 50 | | | | | 55 | | | | | 60 | | | | |
| Ala | His | Tyr | Arg | Asp | Glu | Asp | Gly | Asp | Leu | Val | Ala | Phe | Ser | Ser | Asp |
| 65 | | | | | 70 | | | | | 75 | | | | | 80 |
| Glu | Glu | Leu | Thr | Met | Ala | Met | Ser | Tyr | Val | Lys | Asp | Asp | Ile | Phe | Arg |
| | | | | 85 | | | | | 90 | | | | | 95 | |
| Ile | Tyr | Ile | Lys | Glu | Lys | Lys | Glu | Cys | Arg | Arg | Glu | His | Arg | Pro | Pro |
| | | | 100 | | | | | 105 | | | | | 110 | | |
| Cys | Ala | Gln | Glu | Ala | Pro | Arg | Asn | Met | Val | His | Pro | Asn | Val | Ile | Cys |
| | | 115 | | | | | 120 | | | | | 125 | | | |
| Asp | Gly | Cys | Asn | Gly | Pro | Val | Val | Gly | Thr | Arg | Tyr | Lys | Cys | Ser | Val |
| | 130 | | | | | 135 | | | | | 140 | | | | |
| Cys | Pro | Asp | Tyr | Asp | Leu | Cys | Ser | Val | Cys | Glu | Gly | Lys | Gly | Leu | His |
| 145 | | | | | 150 | | | | | 155 | | | | | 160 |
| Arg | Glu | His | Ser | Lys | Leu | Ile | Phe | Pro | Asn | Pro | Phe | Gly | His | Leu | Ser |
| | | | | 165 | | | | | 170 | | | | | 175 | |
| Asp | Ser | Phe | Ser | His | Ser | Arg | Trp | Leu | Arg | Lys | Leu | Lys | His | Gly | His |
| | | | 180 | | | | | 185 | | | | | 190 | | |
| Phe | Gly | Trp | Pro | Gly | Trp | Glu | Met | Gly | Pro | Pro | Gly | Asn | Trp | Ser | Pro |
| | | 195 | | | | | 200 | | | | | 205 | | | |
| Arg | Pro | Pro | Arg | Ala | Gly | Asp | Gly | Arg | Pro | Cys | Pro | Thr | Ala | Glu | Ser |
| | 210 | | | | | 215 | | | | | 220 | | | | |
| Ala | Ser | Ala | Pro | Pro | Glu | Asp | Pro | Asn | Val | Asn | Phe | Leu | Lys | Asn | Val |
| 225 | | | | | 230 | | | | | 235 | | | | | 240 |
| Gly | Glu | Ser | Val | Ala | Ala | Ala | Leu | Ser | Pro | Leu | Gly | Ile | Glu | Val | Asp |
| | | | | 245 | | | | | 250 | | | | | 255 | |
| Ile | Asp | Val | Glu | His | Gly | Gly | Lys | Arg | Ser | Arg | Leu | Thr | Pro | Thr | Thr |
| | | | 260 | | | | | 265 | | | | | 270 | | |
| Pro | Glu | Ser | Ser | Ser | Thr | Gly | Thr | Glu | Asp | Lys | Ser | Asn | Thr | Gln | Pro |
| | | 275 | | | | | 280 | | | | | 285 | | | |
| Ser | Ser | Cys | Ser | Ser | Glu | Val | Ser | Lys | Pro | Asp | Gly | Ala | Gly | Glu | Gly |
| | 290 | | | | | 295 | | | | | 300 | | | | |
| Pro | Ala | Gln | Ser | Leu | Thr | Glu | Gln | Met | Lys | Lys | Ile | Ala | Leu | Glu | Ser |
| 305 | | | | | 310 | | | | | 315 | | | | | 320 |
| Val | Gly | Gln | Pro | Glu | Glu | Gln | Met | Glu | Ser | Gly | Asn | Cys | Ser | Gly | Gly |
| | | | | 325 | | | | | 330 | | | | | 335 | |
| Asp | Asp | Asp | Trp | Thr | His | Leu | Ser | Ser | Lys | Glu | Val | Asp | Pro | Ser | Thr |
| | | | 340 | | | | | 345 | | | | | 350 | | |
| Gly | Glu | Leu | Gln | Ser | Leu | Gln | Met | Pro | Glu | Ser | Glu | Gly | Pro | Ser | Ser |
| | | 355 | | | | | 360 | | | | | 365 | | | |
| Leu | Asp | Pro | Ser | Gln | Glu | Gly | Pro | Thr | Gly | Leu | Lys | Glu | Ala | Ala | Leu |
| | 370 | | | | | 375 | | | | | 380 | | | | |
| Tyr | Pro | His | Leu | Pro | Pro | Glu | Ala | Asp | Pro | Arg | Leu | Ile | Glu | Ser | Leu |
| 385 | | | | | 390 | | | | | 395 | | | | | 400 |
| Ser | Gln | Met | Leu | Ser | Met | Gly | Phe | Ser | Asp | Glu | Gly | Gly | Trp | Leu | Thr |

-continued 405 410 415

Arg Leu Leu Gln Thr Lys Asn Tyr Asp Ile Gly Ala Ala Leu Asp Thr
420 425 430

Ile Gln Tyr Ser Lys His Pro Pro Pro Leu
435 440

( 2 ) INFORMATION FOR SEQ ID NO:3:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Linker DNA ( i x ) FEATURE:
( A ) NAME/KEY: misc_feature
( B ) LOCATION: 1..21
( D ) OTHER INFORMATION: /label=ATOS-1
/ note="SEQ ID NO: 3 is complementary sequence with SEQ ID No: 4."

( x i ) SEQUENCE DESCRIPTION: SEQ ID NO:3:

CTCTTGCTTG AATTCGGACT A 21

( 2 ) INFORMATION FOR SEQ ID NO:4:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: nucleic acid
( A ) DESCRIPTION: Linker DNA ( i x ) FEATURE:
( A ) NAME/KEY: misc_feature
( B ) LOCATION: 2..21
( D ) OTHER INFORMATION: /label=ATOS-2
/ note="SEQ ID NO: 4 is complementary sequence with SEQ ID NO: 3."

( x i ) SEQUENCE DESCRIPTION: SEQ ID NO:4:

TAGTCCGAAT TCAAGCAAGA GCACA 25

( 2 ) INFORMATION FOR SEQ ID NO:5:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Linker DNA ( i x ) FEATURE:
( A ) NAME/KEY: misc_feature
( B ) LOCATION: 1..21
( D ) OTHER INFORMATION: /label=ATOS-4
/ note="SEQ ID NO: 5 is complementary sequence with SEQ ID NO: 6."

( x i ) SEQUENCE DESCRIPTION: SEQ ID NO:5:

CTCTTGCTTA AGCTTGGACT A 21

( 2 ) INFORMATION FOR SEQ ID NO:6:

-continued ( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: Other nucleic acid
( A ) DESCRIPTION: Linker DNA ( i x ) FEATURE:
( A ) NAME/KEY: misc_feature
( B ) LOCATION: 4..24
( D ) OTHER INFORMATION: /label=ATOS-5
/ note="SEQ ID NO: 6 is complementary sequence with SEQ ID NO: 5."

( x i ) SEQUENCE DESCRIPTION: SEQ ID NO:6:

TAGTCCAAGC TTAAGCAAGA GCACA 25

( 2 ) INFORMATION FOR SEQ ID NO:7:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

Cys Asp Gly Cys Asn Gly Pro Val Val Gly Thr Arg Tyr Lys Cys Ser
1 5 10 15

Val Cys Pro Asp Tyr Asp Leu Cys Ser Val Cys Glu Gly Lys Gly Leu
20 25 30

His Arg Glu His Ser Lys Leu Ile Phe Pro Asn
35 40

( 2 ) INFORMATION FOR SEQ ID NO:8:

( i ) SEQUENCE CHARACTERISTICS:
( A ) LENGTH: 44 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Cys Asp Gly Cys Gly Leu Ala Pro Leu Ile Gly Phe Arg Tyr Lys Cys
1 5 10 15

Val Gln Cys Ser Asn Tyr Asp Leu Cys Gln Lys Cys Glu Leu Ala His
20 25 30

Glu His Pro Glu His Leu Met Leu Arg Met Pro Thr
35 40

( 2 ) INFORMATION FOR SEQ ID NO:9:

( i ) SEQUENCE CHARACTERISTICS:
( A ) LENGTH: 48 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Cys Asp Val Cys Ser Ala Asp Cys Thr Asn Arg Val Arg Val Ser Cys
1 5 10 15

-continued

```
Ala Ile Cys Pro Glu Tyr Asp Leu Cys Val Pro Cys Phe Ser Gln Gly
            20                  25                  30

Ser Tyr Thr Gly Lys His Arg Pro Tyr His Asp Tyr Arg Ile Ile Glu
        35                  40                  45
```

( 2 ) INFORMATION FOR SEQ ID NO:10:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

```
Tyr Asp Leu Cys
1
```

( 2 ) INFORMATION FOR SEQ ID NO:11:

( i ) SEQUENCE CHARACTERISTICS:
( A ) LENGTH: 51 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

```
Ala Asp Pro Arg Leu Ile Glu Ser Leu Ser Gln Met Leu Ser Met Gly
1               5                   10                  15

Phe Ser Asp Glu Gly Gly Trp Leu Thr Arg Leu Leu Gln Thr Lys Asn
            20                  25                  30

Tyr Asp Ile Gly Ala Ala Leu Asp Thr Ile Gln Tyr Ser Lys His Pro
        35                  40                  45

Pro Pro Leu
    50
```

( 2 ) INFORMATION FOR SEQ ID NO:12:

( i ) SEQUENCE CHARACTERISTICS:
( A ) LENGTH: 49 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

```
Thr Asp Glu Ser Ile Asn Lys Ser Ile His Ala Met Met Ala Met Gly
1               5                   10                  15

Phe Ser Asn Glu Gly Ala Trp Leu Thr Gln Leu Leu Glu Ser Val Gln
            20                  25                  30

Gly His Ile Ser Ala Ala Leu Asp Val Met Asn Val Ser Gln Asn Arg
        35                  40                  45

Asn
```

( 2 ) INFORMATION FOR SEQ ID NO:13:

( i ) SEQUENCE CHARACTERISTICS:
( A ) LENGTH: 4 amino acids
( B ) TYPE: amino acid
( C ) STRANDEDNESS: single
( D ) TOPOLOGY: linear -continued ( i i ) MOLECULE TYPE: peptide ( x i ) SEQUENCE DESCRIPTION: SEQ ID NO:13:

Met Gly Phe Ser
1

( 2 ) INFORMATION FOR SEQ ID NO:14:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Ala Ala Leu Asp
1

BONE-ASSOCIATED TRANSCRIPTION CONTROL FACTOR-LIKE PROTEIN

BACKGROUND OF THE INVENTION

1. Field of the Invention

The present invention provides a novel bone-associated protein. More particularly, the protein of the present invention is named OSF-6, and belongs to a group of transcription control factor molecules. In addition, this OSF-6 can be obtained from bone of mammals, including mice and humans. Moreover, the present invention provides a process for producing OSF-6 by recombinant gene technology using cultured cells such as animal cells.

The diseases generally referred to as bone metabolic diseases may include osteoporosis, Paget's disease, osteomalacia, hyperostotic disease, osteopetrosis and the like. Osteoporosis has particularly a high incidence among over approximately half of the population of women after the menopause and older persons; therefore, diagnosis and effective therapy have been strongly required.

Bone metabolic diseases are accompanied with any effects of the metabolism that are specific to bone at the cellular level in bone. It may be a very useful tool for elucidating the abnormal metabolism to discover, isolate and identify the factors capable of specifically participating in bone metabolism. The present inventors have made earnest studies to find out one of the specific factors to such bone metabolism and finally completed the present invention.

In the concrete, the present inventors particularly identified a protein factor specifically produced by a cell line of osteoblast that plays a major role in bone formation. Moreover, the present invention provides a novel essentially bone-specific protein named OSF-6 that was obtained by the said research, and that has strong homology in terms of various previously known transcription control factors at the amino acid level.

The OSF-6 of the present invention is to be produced according to any conventional genetic engineering techniques well-known to those skilled in the art using the DNA sequence as disclosed herein. The OSF-6 or a fragment thereof is to also be produced from the amino acid sequence as disclosed herein according to a chemical peptide synthesis method. Moreover, the partial sequence of the DNA sequence of the present OSF-6 as disclosed herein, which is highly specific to other transcription control factors, is to be synthesized with a 15–50 base length according to a conventional oligonucleotide synthesis method, and it is to be applied as the DNA probe for distinction and diagnosis of bone-derived cells. The distinction of bone-derived cells is useful, especially for distinction of origin of metastatic recurrent cancers, and may thus provide an adequate therapy for recurrent cancers. And further, of the partial peptides of OSF-6, the epitome portion of a peptide capable of recognizing an antibody may be employed for producing a specific monoclonal antibody to OSF-6. The monoclonal antibody thus obtained is useful for the identification of bone-derived cells using an immunological cellular tissue staining method.

The prior findings will be summarized below as reported in regard to the protein of the group of transcription control factors to which the OSF-6 provided by the present invention belongs.

It may be said in higher organisms that the phenomena of cell differentiation or cell development are the results of gene expression intricately regulated, temporally and spatially. Accordingly, it will be important in order to comprehend such life phenomena to elucidate control mechanisms of gene expression. In many cases, gene expression is controlled at the transcription level. It has been elucidated from previous studies on eucaryotes that there are protein transcription control factors which bind specific sequences on DNA and activate the transcription reaction by RNA polymerase. From the fact that homeobox genes essential to morphogenesis like muscle cell differentiation factor MyO D, and some oncogenes, such as jun or fos, encode transcription factors having DNA binding ability, it may be apparent that the transcription control factors could play an important role in proliferation or differentiation of cells, and further in the development of tissue formation at the individual level like their assembly.

It is known by the molecular structures of transcription control factors cloned so far and analysis of the functional domains thereof that typical transcription control factors could have a DNA-binding region and a transcription-activating region, and that they could be classified into some corresponding motives [Mitchel and Tjian, (1989) Science, Vol., 245, pp. 371–378]. The DNA-binding region as classified there mentions a zinc-finger, homeodomain, leucine zipper, and the like. The zinc-finger has a conformation containing $Zn^{2+}$ bound via adjacent 2 cysteine residues and 2 histidine residues, and has been found in many DNA-binding proteins. The homeodomain is the region highly conserved in the homeobox gene product, which plays an important role in morphogenesis, and has the helix-turn-helix structure of approximately 60 amino acids. The leucine zipper has the Leu residues at seven intervals in a helix structure, is lined on the same dimension, and may participate in dimer formation. It is believed that the direct interaction with DNA would be made with the adjacent basic amino acid region. On the other hand, the acidic amino acid region, the glutamic acid-rich region, the proline-rich region and the like, have been reported as the transcription-activating regions as classified. The mechanism to promote transcription in these transcription-activating regions has not yet been elucidated; the recent study using yeast has, however, revealed the direct interaction of the transcription-activating region with the transcription-initiating complex. Moreover, it was suggested that the interaction could be done via the non-DNA binding protein factor called the adaptor or the mediator, and the cDNA cloning of the molecule believed to function actually as the adaptor was performed [Berger et al., (1992) Cell, Vol. 70, pp. 251–265)].

2. Description of the Prior Art

Osteoblasts, which play a major role in the process of bone formation, are considered to differentiate from undifferentiated mesenchymal cells. Although it is also known that these cells are able to differentiate into myoblasts and adipocytes in addition to osteoblasts, there are many aspects that remain unclear in the process in which pre-osteoblasts differentiate into mature osteoblasts. BMPs (bone morphogenetic proteins) (Wozney et al., (1988) Science, Vol. 242, pp. 1528, 1534), which are known bone formation factors, are reported to have the ability to induce differentiation of a certain type of stromal cell line into osteoblast-like cells (Yamaguchi et al., (1991) J. Cell Bio., Vol. 113, pp. 681–687, and Thies et al., (1992) Endocrinology, Vol. 130, pp. 1318–1324). However, the mechanism by which the expression of bone-associated genes is brought about still remains almost unknown. In addition, the differential gene expressions of type I collagen, alkaline phosphatase, as well as other bone matrix proteins such as osteopontin and osteocalcin, are observed in the differentiation process of osteoblasts. The regulation of expression of these genes is considered to be important in the differentiation of osteoblasts, or in other words, in the process of bone formation. For example, known transcription control factors involved in bone formation include a vitamin D receptor, which is bound to the upstream region of the osteopontin or osteocalcin gene and promotes transcription thereof, as well as c-Fos, which is expressed in large amounts in bone and cartilaginous tissues in the generation process. However, there are still no reports of transcription control factors specific to osteoblasts.

BRIEF DESCRIPTION OF THE DRAWINGS

FIG. 2 is a chart comparing the amino acid sequences in the Zn finger-like region of mouse OSF-6, Drosophila Ref(2)P and yeast ADA2 (SEQ ID NOs: 7, 8, 9, and 10). Amino acid residues common to the respective molecules are shown in the form of consensus sequence.

FIG. 3 is a chart comparing the amino acid sequences of the C terminal region of mouse OSF-6 and the region of Drosophila Ref(2)P encoded by the third exon (SEQ ID NOs: 11, 12, 13, and 14). The amino acid residue common to both are shown in the form of a consensus sequence.

DESCRIPTION OF THE INVENTION

Figure 1:
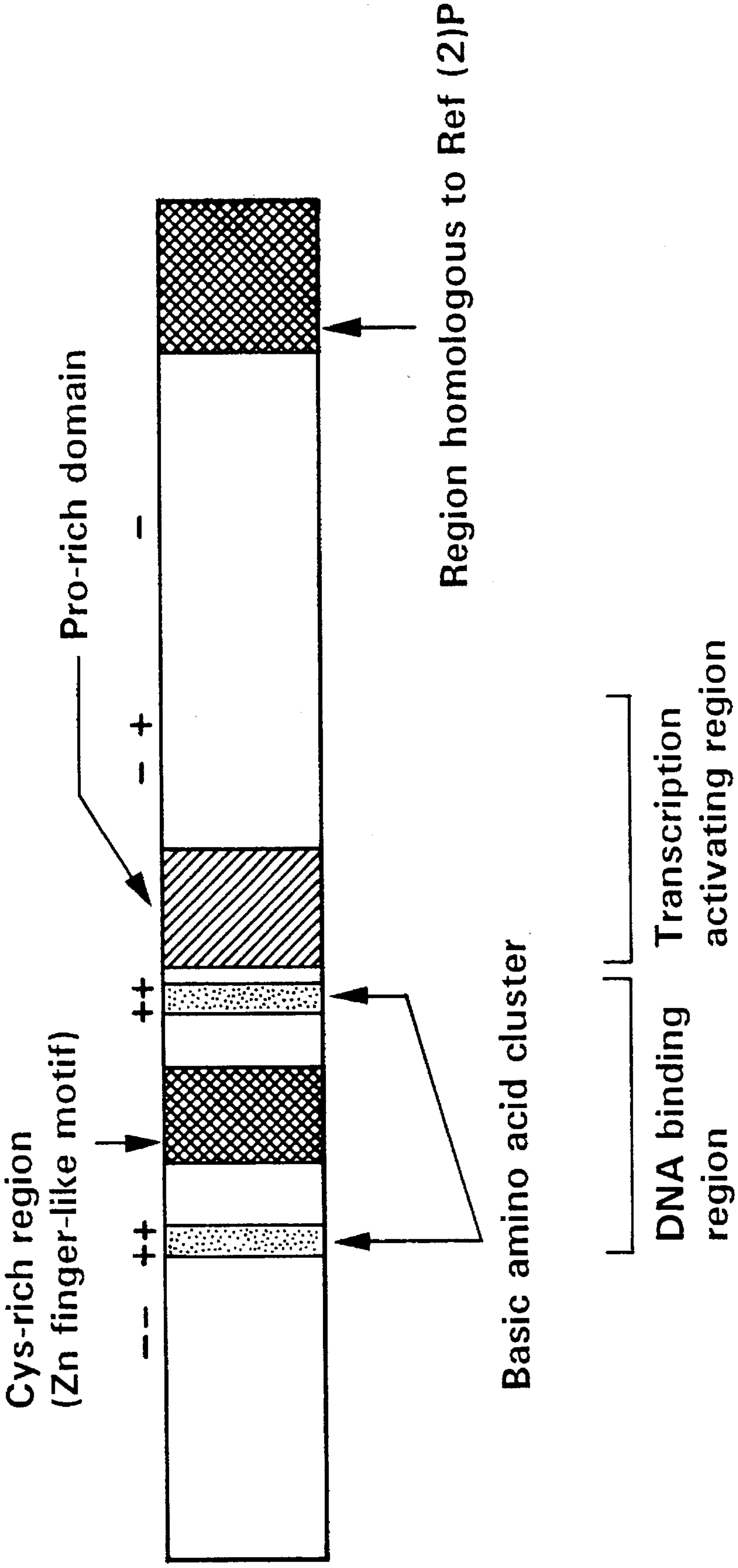
FIG. 1 is a schematic drawing of the structure of mouse OSF-6 protein.

It is, accordingly, an object of the present invention to find out a new type of the transcription control factor which is expressed specifically in bone, inter alia, osteoblasts. Such bone-derived transcription control factor may control the expression of various genes essential for bone formation, mainly in a bone formation period, and thus it may be expected to exert a therapeutic effect on various bone metabolic diseases.

cDNA of mouse OSF-6 was cloned from a cDNA library derived from the mouse osteoblast-like cell line MC3T3-E1 by a differential screening method after preparation of a cDNA library using a combination of both PCR (polymerase chain reaction) method and subtraction method. The resulting clone was named OSF-6 and its cDNA sequence was determined. The cDNA sequence of the OSF-6 was confirmed to be a new sequence as a result of accessing various DNA and amino acid sequence data bases currently available. The cDNA of this invention may be used to isolate other corresponding mammalian genes, especially the human gene, by using it as a hybridization probe under stringent hybridization conditions.

OSF-6 does not have a signal peptide typically known to be possessed by a secretory protein. OSF-6 has a Zn finger-like motif in the region from the 128th cysteine to the 163rd histidine from the N terminal. This cysteine-rich region demonstrates homology with the Drosophila ref(2)P gene product (Dezelee et al., (1989) The EMBO J., Vol. 8, pp. 3437–3446) and yeast ADA2 (Berger et al., (1992) Cell, Vol. 70, pp. 251–265). Although the function of these molecules is not clear, ADA2 is surmised to have the function of a bridging molecule (adaptor) that allows physical interaction between transcription control factors, such as an enhancer binding protein and basic transcription control factors, such as a TATA box binding protein. Two basic amino acid clusters (the position of amino acids 100–110, 181–192) are present on both sides of this region. It has been reported that in the existing DNA binding proteins, the basic amino acid region adjacent to the leucine zipper is directly bound to DNA. Accordingly, there is also a possibility that the corresponding region of OSF-6, as well as the Zn finger-like motif, is involved in DNA binding. A proline-rich domain is present from the position of amino acids 196 to 232. The proline content of this region reaches approximately 30%, and the region is considered to correspond to a transcription activating domain reported in several transcription control factors such as CTF/NF-1. The C terminal region of OSF-6 (the position of amino acids 392–442) demonstrates approximately 40% homology with the domain coded by the third exon of the ref(2)P gene (corresponding to the C terminal of the same Ref(2)P protein), thereby suggesting a functional correlation. OSF-6 is a charged protein that is hydrophilic overall and contains numerous basic or acidic amino acids.

In general, OSF-6 may be extracted directly from bone or cartilaginous tissues according to any well-known biochemical techniques using materials from human beings, bovine, mice, and other animals. The DNA encoding OSF-6 can be obtained by the cDNA library prepared from the mRNA extracted from bone of vertebrates, or the genome gene library, using the labelled fragment of mouse cDNA sequence, as disclosed herein as a probe. The cDNA clone with a full length can be obtained according to the aforesaid techniques or any combination with other standard molecular biological techniques.

Moreover, the present invention provides an analog of OSF-6. Namely, the present invention provides mutants, fusion proteins and fragments that contain OSF-6 and its analog. In addition, the present invention provides a process for producing OSF-6 by recombinant gene technology.

This invention will be illustrated by way of the following Examples.

EXAMPLE 1

Construction of Subtraction/PCR cDNA Library

In this example, there will be disclosed a construction of the cDNA library specific to osteoblast-like cell line MC3T3-E1. The cDNA library is the MC3T3-E1 cDNA library, subtracting the gene expressed in mouse hepatic tissues by combination of a subtraction method with the PCR method, wherein each cDNA clone has a gene fragment with approximately 300 base pairs on average, and further, has a characteristic of amplifying even those genes which originally were at lower levels.

The protocol relating to all general recombinant DNA techniques was performed, unless otherwise indicated, according to "Molecular Cloning Manual" by Sambrook et al. (1989, Cold Spring Harbor Laboratories Inc., U.S.A., Cold Spring Harbor). The total RNA was extracted from $8\times10^7$, approximate 1 g, each of MC3T3-E1 cells and mouse hepatic tissues according to the guanidine method. The poly $A^+$RNA was purified from the total RNA, using the commercially available "oligo dT latex mRNA purification kit" (available from Takara Shuzo K.K.). cDNA was synthesized using 1 μg each of the poly $A^+$RNA as a template and the cDNA synthesis kit (available from Amersham Inc.), provided that a random primer was used, instead of the oligo dT primer, in a 1.5 times larger amount than the usually applied one. Thus, the cDNA strand elongation reaction was restricted to approximately 300 bases on average.

After the double strand was blunt-ended using the above-mentioned kit, the following two types of synthesis DNA linkers were used to ligate ATOS-½ to MC3T3-E1 cDNA and ATOS-⅘ to liver cDNA, respectively, by T4DNA ligase (available from Takara Shuzo KK).

| | |
|---|---|
| ATOS-1/2 | |
| ATOS-1 (SEQ ID NO:3) | 5'- CTCTTGCTTGAATTCGGACTA-3' |
| ATOS-2 (SEQ ID NO:4) | 3'-ACACGAGAACGAACTTAAGCCTGAT-5' |
| ATOS-4/5 | |
| ATOS-4 (SEQ ID NO:5) | 5'- CTCTTGCTTAAGCTTGGACTA-3' |
| ATOS-5 (SEQ ID NO:6) | 3'- ACACGAGAACGAATTCGAACCTGAT-5' |

Thereafter, amplification of DNA for each reaction product was performed according to the PCR (Polymerase Chain Reaction) method using as primers ATOS-1 and ATOS-4, respectively. Concentration of the amplified DNA was measured using a DNA concentration measurement kit, "DNA Dipstick" (available from Invitrogen Inc.). The subtraction method was performed using Photobiotin (available from Pierce Inc.). To 20 μg of the liver cDNA amplified by the PCR method was added 20 ng of Photobiotin, and the DNA was labelled with the biotin by irradiation of a sun lump at a distance of 10 cm for 10 minutes. To 3.0 μg of the labelled liver cDNA was added 0.3 μg of unlabelled MC3T3-E1 cDNA to perform hybridization. Then, Streptavidin (available from Takara Shuzo K.K.) was allowed to react and extraction with phenol was performed to remove the cDNA common to liver cDNA from the MC3T3-E1 cDNA. The subtraction method was again repeated to remove the cDNA common to liver cDNA from the MC3T3-E 1 cDNA as far as possible. And further, the remaining DNA was amplified according to the PCR method, using the said ATOS-1, and the DNA concentration was measured. 10 ng of the cDNA was digested with the restriction enzyme EcoRI, and ligated with 1 μg of phage vector λgt 10 (λgt 10/EcoRI cloning kit, available from Stratagene Inc.), of which the terminal was digested with EcoRI and dephosphorylated using T4 ligase. It was packaged to λ phage particles using the commercially available in vitro packaging kit, "Gigapack-gold" (available from Stratagene Inc.). The recombinant phage was infected to E. coli C600 (stored as HT003 in the National Institute of Health and the Cancer Research Institute, Source Bank, Japan), mixed with the soft agar cultured broth, and added over an agar medium to form phage plaque. Infection efficacy was measured to give a phage plaque titer of $3\times10^6$/1 μg cDNA.

Next, the highly specific clone to MC3T3-E1 was selected from the cDNA library using a differential screening method. More specifically, $2.25\times10^4$ phages were spread onto a total of 10 plates and then transferred onto respective 2 nylon membrane filters each (a total of 20 filters). Of them, hybridization was performed using the radiolabelled MC3T3-E1 cDNA as one probe and similarly labelled liver cDNA as another-probe. 273 clones, wherein signals were observed with the MC3T3-E1 cDNA probe and no signals were observed with the liver cDNA probe, were employed as a minilibrary for subsequent experiments.

EXAMPLE 2

Isolation of Mouse OSF-6 Clone

In this example, there will be disclosed the method wherein the partial cDNA fragment of OSF-6 is identified as a specific clone to MC3T3-E1 from the minilibrary prepared as described in the above Example 1, and then, a full length cDNA is cloned from the cDNA library of MC3T3-E1 using the fragment. 1 μg of the total RNA of the MC3T3-E1 and liver, prepared as described in Example 1, were spotted onto a nylon membrane filter, and 273 filters were prepared to be used for the following hybridization. On the other hand, the DNA at the insertion site of the 273 phage clones, prepared as described in Example 1, was amplified using the PCR method. After the DNA was subjected to agarose gel electrophoresis, the main bands were excised, purified and radio-labelled to prepare probes. For the clones wherein signals were observed with MC3T3-E1 and no signals were observed with liver as the results of autoradiography, recloning to a plasmid vector was performed. Namely, the insertion fragments that were amplified by the PCR method and purified were digested with the restriction enzyme EcoRI and recloned into the EcoRI site of the plasmid vector pUC118 (available from Takara Shuzo K.K.). The cDNA sequences for these clones were determined with a universal primer using a commercially available "DNA sequencing kit" (available from Takara Shuzo K.K.). Examination of the resulting cDNA sequence upon the DNA and protein databases revealed a novel clone, which is not identical to the previous DNA and protein and named pMCLS 6. Subsequent cloning of full length cDNA was performed using the clone, For full length cDNA cloning, the double strand cDNA with blunt ends was synthesized from 5 μg of the poly $A^+$RNA of the MC3TC-E1 purified as described in Example 1, using "cDNA synthesis system plus" (Amersham Inc.). After the EcoRI/NotI adaptor (available from Takara Shuzo K.K.) was ligated with the cDNA using T4 ligase, agarose gel electrophoresis was performed to purify those fractions having not less than approximately 700 base pairs. The fragment was ligated with λgt 10 phage vector (available from Stratagene Inc.) at the EcoRI site, packaged in the similar manner as described in Example 1, and infected to E. coil. Infection efficacy was measured to be $1.5\times10^7$/1 μg vector DNA. The pMCLS 6 was radio-labelled and applied as a probe, whereby $1.0\times10^6$ phage clones of the cDNA library was subjected to screening according to a plaque hybridization method. As a result, 11 positive clones were finally obtained. Agarose gel electrophoresis of these phage DNA digested with EcoRI revealed that two EcoRI sites were present in the insertion fragment. Then, the three EcoRI fragments (approximately 1.7 kb, 0.15 kb and 0.2 kb) of the phage clone having the longest insertion fragments were recloned to the plasmid vector pUC118 (available from Takara Shuzo K.K.) separately at the EcoRI site, which were named pKOT97, pKOT105 and pKOT109, respectively. On the other hand, in order to determine the cDNA sequence at the linked site of each EcoRI fragment, the BglII-Hind III fragment of the OSF-6 cDNA-containing phage was cloned to pUC118 at the BamHI-Hind III site. Further, the PstI-Sac I fragment (approximately 1.3 kb, containing approximately 0.9 kb of the phage-derived DNA), which contained two EcoRI sites of OSF-6 cDNA from the plasmid, was subcloned to pUC118, which was named pKOT103.

EXAMPLE 3

DNA Sequence of Mouse OSF-6

Figure 4:
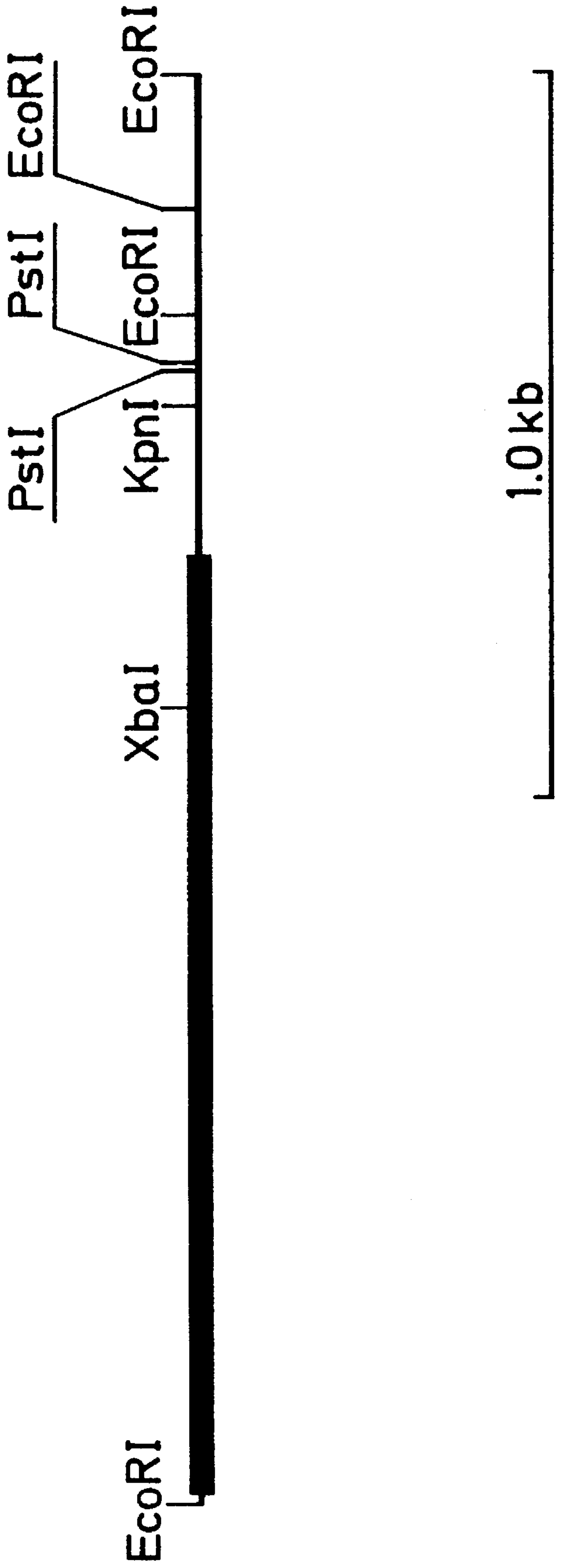
FIG. 4 is a restriction enzyme map of cDNA coding for mouse OSF-6. The bold line indicates the coding region of OSF-6 cDNA.
Figure 5:
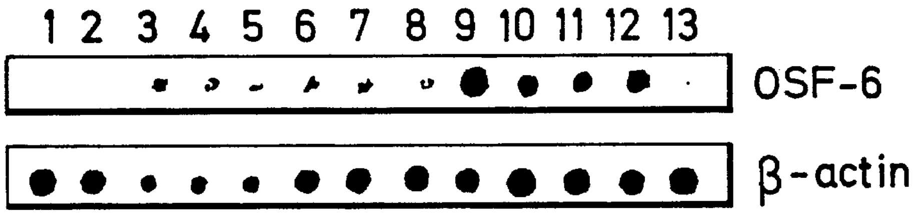
FIG. 5 shows the tissue-specific expression of mouse OSF-6. This was analyzed by RNA dot blotting using RNA from various tissues and cultured cells. The diagram shows the results of autoradiography.

The deletion mutants from both directions at the respective intervals of approximate 300 base pairs were prepared from the subclone having pKOT97 and its cDNA fragment, using "Kilosequence deletion kit" (available from Takara Shuzo K.K.). Determination of the cDNA sequence of the respective deletion mutants was performed using the automatic DNA sequencer model 373A (available from Applied Biosystems Co., Ltd., U.S.A.). Determination of the cDNA sequence of the subclone having pKOT103, pKOT105, pKOT109 and their cDNA fragments was also performed in the same manner as described above. The full length cDNA sequence obtained by linking them and the amino acid sequence translated from the cDNA sequence are shown in SEQUENCE ID No. 1 and SEQUENCE ID No. 2 in the sequence listing. The protein encoded in the cDNA was named mouse OSF-6. The amino acid residue No. 1 does correspond to the N-terminal of the estimated mouse OSF-6 protein. Also, the schematic drawing of the structure of the estimated protein is shown in FIG. 1, and the restriction enzyme map of the cDNA is shown in FIG. 4. According to the examination of the cDNA sequence and amino acid sequence of OSF-6 thus obtained upon DNA and protein databases now available, the OSF-6 was proven to be a novel protein which shows a partial homology with drosophila Ref(2)P and yeast ADA2.

EXAMPLE 4

Tissue-specific Expression of Mouse OSF-6

In order to investigate tissue specificity in expression of mouse OSF-6, RNA dot blotting was performed. Total RNA of thymus, spleen, brain, kidney, lung, testis or heart was prepared from mice (available from Nihon Kurea) according to the guanidine method. The cells containing abundantly osteoblasts were prepared from the primary culture of calvaria cells of newborn mice. Then, total RNA was extracted from the cells in the same manner as described above. Each total RNA (1 μg) of the above tissues, cultured calvaria cells, MC3T3-E1 and mouse fibroblast cell line NIH3T3 (ATCC CRL 1658) was dotted on a nylon membrane filter (Biodyne: PALL Co., Ltd.), immobilized by heating, and then applied for hybridization. On the other hand, pKOT97 was digested with EcoRI, and the 1.7 kb fragment was separated, purified by agarose gel electrophoresis, and labelled with isotope to employ as a probe. As a result of autoradiography, the primary culture of calvaria cells and MC3T3-E1 showed strong signals, while weak signals were observed in brain, kidney and testis. The expression level in MC3TC-E1 was increased as the culture period was prolonged. (The strongest expression was observed in the cells after 60 days incubation.).

EXAMPLE 5

Expression of OSF-6 in Escherichia Coli and Preparation of Anti- Mouse OSF-6 Antiserum The coding region of mouse OSF-6 cDNA could be expressed in a large amount in E. coil as a fusion protein with GST (glutathion-S-transferase) or lacZ by cloning into a commercially available vector for expression in E. coil such as pGEX. The fusion protein expressed could be purified according to a general biochemical technique. The recombinant OSF-6 protein thus produced could be used as an antigen for the preparation of an anti-OSF-6 antibody.

EXAMPLE 6

Expression of OSF-6 in Animal Cells

The NotI fragment (2.0 kb) containing the full length mouse OSF-6 cDNA could be cloned into a suitable expression vector for animal cells and introduced and expressed in CHO (Chinese Hamster Ovary) using a conventional transfection method such as the calcium phosphate coprecipitation method. The gene-transduced cells could be selected and cloned by using such drug resistant genes as $neo^r$ and the like. The cells thus established could be used for the production of OSF-6 in animal cells and others.

We claim:

1. An isolated and purified protein comprising OSF-6, having the amino acid sequence from no. 1 to no. 442 in (SEQ NO: 2) of the sequence tables.

* * * * *